United States Patent
Becker et al.

(10) Patent No.: US 11,207,611 B1
(45) Date of Patent: Dec. 28, 2021

(54) PROCESS FOR SEPARATING HYDROCARBONS IN A LIQUID FEED UTILIZING AN EXTERNALLY HEATED REBOILER CONNECTED TO A DIVIDED WALL COLUMN AS THE PRIMARY SOURCE OF HEAT ENERGY

(71) Applicant: BURNS & McDONNELL ENGINEERING COMPANY, INC., Kansas City, MO (US)

(72) Inventors: Andrew Becker, Westwood, KS (US); Curt Hemphill, Overland Park, KS (US); Christopher Niemeyer, Kingwood, TX (US); Edward McCoy, Overland Park, KS (US)

(73) Assignee: BURNS & MCDONNELL ENGINEERING COMPANY, INC., Kansas City, MO (US)

( * ) Notice: Subject to any disclaimer, the term of this patent is extended or adjusted under 35 U.S.C. 154(b) by 74 days.

(21) Appl. No.: 16/459,894

(22) Filed: Jul. 2, 2019

Related U.S. Application Data (60) Provisional application No. 62/693,638, filed on Jul. 3, 2018.

(51) Int. Cl.
| | |
|---|---|
| *B01D 3/14* | (2006.01) |
| *C10G 7/00* | (2006.01) |
| *C07C 7/04* | (2006.01) |
| *B01D 5/00* | (2006.01) |
| *B01D 3/32* | (2006.01) |
| *B01D 3/00* | (2006.01) |

(52) U.S. Cl.
CPC ............. *B01D 3/141* (2013.01); *B01D 3/007* (2013.01); *B01D 3/32* (2013.01); *B01D 5/006* (2013.01); *B01D 5/0039* (2013.01); *B01D 5/0075* (2013.01); *C07C 7/04* (2013.01); *C10G 7/00* (2013.01); *C10G 2300/1025* (2013.01); *C10G 2400/28* (2013.01)

(58) Field of Classification Search
None
See application file for complete search history.

(56) References Cited

U.S. PATENT DOCUMENTS

| | | | |
|---|---|---|---|
| 3,034,307 A * | 5/1962 | Berger | ............... B01D 3/4227 62/628 |
| 4,230,533 A | 10/1980 | Giroux | |
| 4,773,968 A | 9/1988 | O'Connell et al. | |
| 5,457,277 A | 10/1995 | Sy | |
| 6,077,985 A | 6/2000 | Stork | |
| 6,291,734 B1 | 9/2001 | Stork | |
| 6,347,533 B1 | 2/2002 | Tung | |
| 6,540,907 B1 | 4/2003 | Towler et al. | |

(Continued)

FOREIGN PATENT DOCUMENTS

WO  WO 2016128110 A1  8/2016

*Primary Examiner* — Derek N Mueller
(74) *Attorney, Agent, or Firm* — Stinson LLP (57) ABSTRACT

The present invention is directed to a system and process for fractionating a hydrocarbon liquid feed using a single dividing wall column (DWC), an externally heated reboiler connected to the DWC, and a deisobutanizer (DIB) integrated with a compressor. The majority of all externally supplied heat energy supplied to the system is input to the system via the externally heated reboiler of the DWC.

13 Claims, 3 Drawing Sheets

(56) References Cited

U.S. PATENT DOCUMENTS

| | | |
|---|---|---|
| 6,551,465 B1 | 4/2003 | Van Zile et al. |
| 6,726,835 B2 | 4/2004 | Towler et al. |
| 6,927,314 B1 | 8/2005 | Schultz et al. |
| 7,169,267 B2 | 1/2007 | Kaibel et al. |
| 7,249,469 B2 | 7/2007 | Porter |
| 7,264,696 B2 | 9/2007 | Kaibel et al. |
| 7,422,197 B2 | 9/2008 | Zone et al. |
| 7,437,891 B2 | 10/2008 | Reyneke et al. |
| 7,462,277 B2 | 12/2008 | Adrian et al. |
| 7,528,290 B2 | 5/2009 | Zimmermann et al. |
| 7,556,717 B2 | 7/2009 | Heida |
| 7,649,108 B2 | 1/2010 | Schal et al. |
| 7,691,239 B2 | 4/2010 | Kister et al. |
| 7,763,165 B1 | 7/2010 | Schultz |
| 8,007,661 B1 | 8/2011 | Schultz et al. |
| 8,092,655 B2 | 1/2012 | Burst et al. |
| 8,178,060 B2 | 5/2012 | Corradi |
| 8,323,457 B2 | 12/2012 | Townsend |
| 8,480,860 B2 | 7/2013 | Kovak |
| 8,562,792 B2 | 10/2013 | King |
| 8,747,654 B2 | 6/2014 | Ulas et al. |
| 8,771,479 B2 | 7/2014 | Lee et al. |
| 8,845,864 B2 | 9/2014 | Lee et al. |
| 9,309,169 B2 | 4/2016 | Ou et al. |
| 9,504,934 B2 | 11/2016 | Agrawal et al. |
| 9,683,776 B2 | 6/2017 | Stylianou et al. |
| 9,724,619 B2 | 8/2017 | Bhargava et al. |
| 9,895,624 B2 | 2/2018 | Lee et al. |
| 9,938,205 B2 | 4/2018 | Du et al. |
| 10,005,002 B2 | 6/2018 | Gao et al. |
| 10,106,476 B1 | 10/2018 | Kockler |
| 2007/0227875 A1 | 10/2007 | Kammerhofer |
| 2012/0141333 A1 | 6/2012 | Ulas et al. |
| 2012/0149957 A1 | 6/2012 | Krupa et al. |
| 2013/0213088 A1* | 8/2013 | Stylianou ............ C10L 3/101 62/630 |
| 2014/0171717 A1* | 6/2014 | Sinha .................. B01D 3/143 585/802 |
| 2014/0231238 A1 | 8/2014 | Bhargava et al. |
| 2014/0262740 A1 | 9/2014 | McCaulley |
| 2015/0041308 A1 | 2/2015 | Lee et al. |
| 2015/0052938 A1 | 2/2015 | Bauer et al. |
| 2015/0251972 A1 | 9/2015 | Shecterle et al. |
| 2016/0102032 A1 | 4/2016 | Du et al. |
| 2017/0029348 A1 | 2/2017 | Bender |
| 2017/0239589 A1 | 8/2017 | Spriewald |
| 2018/0154278 A1 | 6/2018 | Lee et al. |
| 2018/0178141 A1 | 6/2018 | Lee et al. |
| 2018/0216011 A1 | 8/2018 | Phu |

* cited by examiner

PROCESS FOR SEPARATING HYDROCARBONS IN A LIQUID FEED UTILIZING AN EXTERNALLY HEATED REBOILER CONNECTED TO A DIVIDED WALL COLUMN AS THE PRIMARY SOURCE OF HEAT ENERGY

CROSS-REFERENCE TO RELATED APPLICATIONS

This application is based on and claims priority to U.S. Provisional Application Ser. No. 62/693,638, filed on Jul. 3, 2018, which is incorporated herein by reference in its entirety.

STATEMENT REGARDING FEDERALLY SPONSORED RESEARCH OR DEVELOPMENT

Not applicable.

STATEMENT REGARDING JOINT RESEARCH AGREEMENT

Not applicable.

BACKGROUND OF THE INVENTION

1. Field of the Invention

The present invention is generally directed to the field of separating hydrocarbons in a liquid feed stream, and is more particularly directed to a system and process for fractionating a hydrocarbon liquid feed stream utilizing a single dividing wall column (DWC), an externally heated reboiler connected to the DWC, and a deisobutanizer integrated with a compressor.

2. Description of Related Art

Natural gas liquid (NGL), a type of hydrocarbon liquid feed stream, contains C2+ hydrocarbons separated from the raw natural gas (NG) off the well heads in gas processing plants. NGL is typically sent to fractionation facilities where the ethane, propane, isobutane, n-butane, and C5+ components are separated from one another. The ethane, propane, isobutane and n-butane components (C2-C4) are commonly sold for use as purity products and the C5+ component (natural gasoline) is sold as a low octane gasoline blend stock, diluent, or as a chemical feed such as feed to a steam cracker to produce ethylene, propylene, and other cracking byproducts. The amount, if any, of ethane in any given NGL fractionation feed will vary greatly depending on the region/market, equipment limitations, and pipeline specifications. For example, some gas plants may reject ethane into the mostly methane natural gas stream such that essentially no ethane is contained in the NGL fractionation feed stream, while others recover the ethane into the NGL feed or fractionate ethane out into a relatively pure ethane product using a deethanizer. In addition, some NGL fractionation feed streams carry a very low ethane concentration (such as in the northeast), while others have high ethane concentrations (such as seasonally in the gulf coast).

The NGL fractionation industry in the US has seen a significant growth through the 2000s with the application of horizontal drilling and fracturing technologies sparking significant investment and more NGL production and fractionation. As new fractionation trains are designed and brought on line in this industry, it is desirable for operating companies to try to minimize capital investment, required plot space, and operating expenses. This is often achieved by adding fractionation trains to existing facilities to leverage existing infrastructure with access to NGL feed and underground storage for the storage of purity product(s).

Existing NGL fractionation trains commonly employ a series of fractionation columns (deethanizer, depropanizer, debutanizer, and deisobutanizer (DIB)), each producing a purity product. These multiple fractionation units require significant capital costs to construct and operate; can require a large area of plot space; and can require an increased number of personnel to operate, which in turn increases the potential for injuries. While a variety of different alternative NGL fractionation train configurations have been suggested in the art, a need remains in the art for more cost-effective NGL fractionation trains that can be employed in new facilities or in modifications to existing facilities.

BRIEF SUMMARY OF THE INVENTION

The present invention is directed to a system and process for fractionating a liquid feed that includes hydrocarbons ("hydrocarbon liquid feed") into one or more purity products, wherein the system and process utilize a dividing wall column (DWC) having one or more dividing walls, an externally heated reboiler connected to the DWC, and a deisobutanizer (DIB) integrated with a compressor. The majority of all externally supplied heat energy supplied to the system is input to the system via the externally heated reboiler of the DWC. In a preferred embodiment, at least 95% of all externally supplied heat energy supplied to the system for the primary purpose of fractionation of the hydrocarbon in the hydrocarbon liquid feed is input to the system via the externally heated reboiler of the DWC. In another preferred embodiment, at least 75% of all externally supplied heat energy supplied to the system for any and all purposes is input to the system via the externally heated reboiler of the DWC. By inputting the majority of all externally supplied heat energy to the system via the externally heated reboiler of the DWC, the system and process are much more energy efficient and cost effective than prior art systems and processes using externally heated reboilers for each column.

In a system according to a preferred embodiment of the invention, the DWC is connected to: an inlet for feeding the hydrocarbon liquid feed into the DWC; an overhead outlet through which an overhead comprising C3 hydrocarbons may be removed from the DWC; an intermediate outlet through which an intermediate comprising C4 hydrocarbons may be removed from the DWC and fed to the DIB; a reboiler outlet and inlet connected to the externally heated reboiler of the DWC through which at least a portion of the bottoms in the DWC may be circulated to supply heat to the DWC; and a bottoms outlet through which a bottoms comprising C5+ hydrocarbons may be removed from the DWC as a product. The overhead outlet from the DWC may be connected to a condenser configured to condense the overhead vapor, preferably using water, air, or a combination thereof. The condenser may be connected to a condensed overhead outlet though which at least a portion of the condensed overhead can be refluxed back to the DWC and through which the remaining condensed overhead may be removed as a propane product.

In this system according to a preferred embodiment of the invention, the DIB is connected to: an overhead outlet through which an overhead comprising iso-C4 may be removed from the DIB; a heat exchange outlet and inlet through which at least a portion of the bottoms of the DIB may be circulated through a heat exchange reboiler and returned to the DIB; and a bottoms outlet through which a bottoms comprising n-C4 may be removed as an n-butane product. The compressor is connected to the DIB overhead outlet and configured to compress the overhead exiting the DIB overhead outlet and to feed the compressed overhead through the heat exchange reboiler so as to condense the DIB overhead and heat the bottoms circulating through the heat exchange reboiler to supply heat to the DIB. The heat exchange reboiler eliminates the need for an externally heated reboiler (in addition to the externally heated reboiler connected to the DWC) connected to the DIB to heat the bottoms of the DIB. The heat exchange reboiler may be connected to a condensed overhead outlet through which a portion of the condensed overhead can be refluxed back to the DIB and through which the remaining condensed overhead comprising iso-C4 may be removed as an isobutane product.

Where the hydrocarbon liquid feed comprises C2+ hydrocarbons and there is a desire to produce an ethane product, the system in accordance with a preferred embodiment may additionally include a deethanizer column thermally coupled with other components of the system. In an exemplary embodiment, the deethanizer is thermally coupled with the externally heated reboiler via the dividing wall column (DWC) such that the externally supplied heat input to the system via the externally heated reboiler of the DWC supplies the heat needed for operation of the deethanizer. The deethanizer does not need or have a separate externally heated reboiler dedicated to supplying heat directly to the deethanizer. In this embodiment, the deethanizer is connected to: an inlet for feeding the hydrocarbon liquid feed into the deethanizer; an overhead outlet through which an overhead comprising C2 hydrocarbons may be removed from the deethanizer; and a bottoms outlet through which a bottoms comprising C3+ hydrocarbons is fed from the deethanizer into the DWC. The overhead outlet from the deethanizer may be connected to a condenser configured to condense the overhead, preferably using a refrigerant. The condenser may be connected to a condensed overhead outlet though which at least a portion of the condensed overhead can be refluxed back to the deethanizer and through which the remaining condensed overhead comprising C2 hydrocarbons may be removed as an ethane product. The DWC is connected to a vapor outlet that extends from the DWC to the bottom section of the deethanizer. The vapor outlet is configured to supply heat in the form of vapor from the DWC to the deethanizer.

Where the hydrocarbon liquid feed comprises C2+ hydrocarbons and there is a desire to produce an ethane product, an alternative system in accordance with a preferred embodiment utilizes the DWC (preferably having two dividing walls) as a deethanizer, in addition to serving as a depropanizer and debutanizer. In this embodiment, the DWC is additionally connected to a second overhead outlet through which overhead comprising C2 hydrocarbons may be removed from the DWC. This second overhead outlet may be connected to a condenser configured to condense the overhead, preferably using a refrigerant. The condenser may be connected to a condensed overhead outlet though which at least a portion of the condensed overhead can be refluxed back to the DWC and through which the remaining condensed overhead comprising C2 hydrocarbons may be removed as an ethane product.

In a process according to a preferred embodiment of the invention, the hydrocarbon liquid feed includes one or more C3+ hydrocarbons, and more preferably includes propane (C3), butanes (C4), and C5+ hydrocarbons. In some embodiments, the hydrocarbon liquid feed also includes ethane (C2) in sufficient quantities to produce an ethane product. The process includes the following steps: feeding the hydrocarbon liquid feed to the DWC; heating at least a portion of the bottoms of the DWC via the external heat supply of the externally heated reboiler of the DWC to heat the DWC; feeding an intermediate comprising C4 hydrocarbons from the DWC into the DIB; compressing an overhead vapor of the DIB and feeding the compressed overhead via a compressor through the heat exchange reboiler to condense the overhead; circulating at least a portion of the bottoms of the DIB through the heat exchange reboiler and returning the heated bottoms to the DIB to supply heat to the DIB; and recovering one or more products from the DWC and/or DIB, wherein the products are relatively pure C3-C5+ hydrocarbons and/or one or more combinations of those hydrocarbons.

The process preferably includes recovering an overhead comprising C3 hydrocarbons from the DWC as a propane product; recovering the bottoms comprising C5+ hydrocarbons from the DWC as a C5+ product; recovering the overhead comprising iso-C4 from the DIB as an isobutane product; and/or recovering the bottoms comprising n-C4 from the DIB as an n-butane product. In addition, recovering the overhead comprising C3 hydrocarbons from the DWC as a propane product preferably includes condensing the DWC overhead with a condenser using water, air and/or combinations thereof; optionally returning a portion of the overhead to the DWC as reflux; and removing the remaining condensed overhead as a propane product.

In preferred embodiments, the propane product has a purity of at least about 85%, most preferably at least about 95%; the C5+ product has a purity of at least about 90%, most preferably at least about 98%; the isobutane product has a purity of at least about 90%, most preferably at least about 96%; and/or the n-butane product has a purity of at least about 90%, most preferably at least about 94%.

Where the hydrocarbon liquid feed includes C2+ and there is a desire to produce an ethane product, the process may utilize a deethanizer to recover an ethane product from the hydrocarbon liquid feed. This process additionally includes feeding the hydrocarbon liquid feed containing C2 hydrocarbons to the deethanizer column; recovering a deethanizer overhead comprising C2 hydrocarbons from the deethanizer column as an ethane product; feeding a deethanizer bottoms comprising C3+ hydrocarbons to the DWC; and heating the deethanizer via thermally coupling the deethanizer with the externally heated reboiler of the DWC. The step of recovering the overhead comprising C2 hydrocarbons from the deethanizer as an ethane product may include condensing the deethanizer overhead with a condenser, preferably using a refrigerant; optionally returning a portion of the condensed overhead to the deethanizer as reflux; and removing the remaining condensed overhead as an ethane product. In addition, the step of heating the deethanizer preferably includes feeding a vapor from the DWC to a bottom portion of the deethanizer to thereby heat the deethanizer. The ethane product recovered preferably has a purity of at least about 70%, most preferably at least about 95%.

In an alternative embodiment where the dividing wall column serves as a deethanizer as well as a depropanizer and debutanizer, the hydrocarbon liquid feed fed into the DWC contains C2+ hydrocarbons, and the process additionally includes recovering a second overhead comprising C2 hydrocarbons from the DWC as an ethane product. The step of recovering the second overhead as an ethane product may include condensing the second overhead with a condenser, preferably using a refrigerant; optionally returning a portion of the condensed overhead as reflux to the DWC; and removing the remaining condensed overhead as the ethane product. The ethane product preferably has a purity of at least about 70%, most preferably at least about 95%.

The process and system of the present invention is both energy and cost-effective. The plot space needed for the fractionation train is reduced as compared to prior art systems using a larger number of distillation towers and/or using externally heated reboilers on multiple columns for providing the heat needed by the system for the fractionation. The reduction in equipment needed may also result in safety advantages due to the fact that fewer operators and maintenance personnel may be required. Moreover, the reduction in the hydrocarbon inventory stored within the fractionation train at any given time could also enhance the safety of the system. The heat energy input to the system is primarily attributable to the externally heated reboiler of the DWC, as opposed to less efficient systems using multiple externally heated reboilers. Given that all or a portion of the DWC may be operated at a pressure sufficient to allow cooling air or water to be used to condense the C3 overhead, more expensive refrigerants are not required to produce the propane product. In addition, given that the thermally coupled deethanizer and/or DWC operate at relatively low pressure such that refrigeration may be required to condense the C2 overhead product, some embodiments of the invention are particularly well adapted for production of a fully liquefied ethane product at low pressure for storage or export.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF EXEMPLARY EMBODIMENTS

The liquid feed containing hydrocarbons ("hydrocarbon liquid feed") that is fractionated in accordance with the present invention may be any liquid feed having one or more hydrocarbon constituents to be separated from the liquid feed. The hydrocarbon liquid feed preferably includes one or more C3+ hydrocarbons and may optionally also include C2 (ethane) and may include other trace constituents, including but not limited to methane, water, sulfur, and carbon dioxide. In the exemplary embodiments described herein, the hydrocarbon liquid feed includes C3 (propane), C4 (butane) and C5+ components. The hydrocarbon liquid feed anticipated for use in the first and third exemplary embodiments described herein also additionally includes C2 (ethane). In certain exemplary embodiments, the hydrocarbon liquid feed is a natural gas liquid feed obtained from natural gas well-heads (NGL). A NGL feed will typically have the following composition ranges for C1-C5+ hydrocarbons: C1 (<1.5% liquid volume (LV) of NGL feed); C2 (10-60% LV of NGL feed); C3 (40-65% LV of all C3+ in NGL Feed); i-butane (5-20% LV of all C3+ in NGL feed); n-butane (10-40% LV of all C3+ in NGL feed); C5+ (10-35% LV of all C3+ in NGL feed).

In each of the exemplary embodiments of the invention described herein, a fractionation train consisting of two or more connected fractionation columns, including a dividing wall column (DWC) and a deisobutanizer (DIB) column, are utilized to fractionate the hydrocarbon liquid feed. The majority of all externally supplied heat energy supplied to the system is input to the system via the externally heated reboiler of the DWC. The following definitions and descriptions apply to each of the exemplary embodiments described herein, unless otherwise indicated.

As used herein, the term "butane" can refer to both normal butane (n-butane) or n-C4 and isobutane (i-butane) or i-C4. In the embodiments described herein, the C2, C3, n-C4, i-C4, and C5+ hydrocarbon components of the hydrocarbon liquid feed are recovered as separate relatively pure products, however it should be understood that the invention can encompass the recovery of mixtures of these components. As used herein, the term "column" refers to any system, device, or combination of systems and/or devices suitable for the selective separation of a mixture containing two or more components having differing boiling points. Such columns can include, but are not limited to, scrub columns, distillation columns, rectification columns, and stripping columns as are known in the art. It should be understood that the columns can include a shell or housing disposed at any angle, in any configuration, and/or having any length to diameter (L/D) ratio. For clarity and ease of description, the columns will be further described in this detailed description with reference to a vertical, cylindrical, column having a L/D ratio of greater than 1.

Each column can be empty, partially filled, or completely filled with one or more trays and/or packing materials to improve mass transfer and/or separation of the feed components. The fill material and fill pattern in the columns may vary in the different columns. For example, the fill material in one column can include one or more structured and/or random packed materials while the fill material in another column can include one or more trays. Also for example, the fill material in one fractionation zone of a dividing wall column can include one or more structured and/or random packed materials while the fill material in another fractionation zone of the dividing wall column can include one or more trays. Two or more types of fill material can be disposed in the fractionation columns. For example, a fractionation zone of a column can contain random dumped packing beneath a feed introduction line or column inlet and one or more trays above the column inlet. One or more chimney trays or other liquid trap-out device can be disposed in a fractionation zone of a fractionation column to improve or aid in the withdrawal of a product.

As used herein, the term "trays" includes any type of tray or similar structure that improves the contact between gas and liquid phases within the column. Trays deemed acceptable for purposes of the present invention include, but are not limited to, perforated trays, sieve trays, bubble cap trays, floating valve trays, fixed valve trays, cross-flow trays, radial flow trays, multi-downcomer trays, dual flow trays, baffle trays, snap-in valve trays, chimney trays, slit trays, any high-capacity trays or any combination thereof.

As used herein, the term "packing material" includes any type of structured and/or random shaped material disposed within a column. The packing material can increase the effective surface area within a column, which can improve the mass transfer between liquid and gas phases within a column. The packing material can be made of any suitable material, for example metals, non-metals, polymers, ceramics, glasses, or any combination thereof. Random packing material deemed acceptable for purposes of the present invention can include, but is not limited to, Raschig rings, Lessing rings, I-rings, NeXRing, saddle rings, Intalox saddles, Intalox Ultra, Tellerettes, Pall rings, U-rings, or any combination thereof. Structured packing deemed acceptable for purposes of the present invention can include, but is not limited to corrugated sheets, crimped sheets, gauzes, grids, wire mesh, monolith honeycomb structures, or any combination thereof. Each column can be empty, partially filled, or completely filled with one or more trays and/or packing materials to improve mass transfer and/or separation of the feed components. The fill material and fill pattern in the columns may vary in the different columns. For example, the fill material in one column can include one or more structured and/or random packed materials while the fill material in another column can include one or more trays. Also for example, the fill material in one fractionation zone of a dividing wall column can include one or more structured and/or random packed materials while the fill material in another fractionation zone of the dividing wall column can include one or more trays. Two or more types of fill material can be disposed in the fractionation columns. For example, a fractionation zone of a column can contain random dumped packing beneath a feed introduction line or column inlet and one or more trays above the column inlet. One or more chimney trays or other liquid trap-out device can be disposed in a fractionation zone of a fractionation column to improve or aid in the withdrawal of a product.

Each column can be made of one or more metallic and/or non-metallic materials physically and chemically compatible with the temperature, pressure, and contents of the column. Suitable metallic materials for purposes of the present invention include, but are not limited to, ferrous alloys including carbon and stainless steels.

As used herein, the term "dividing wall column" refers to any column having one or more dividing walls. As used herein, the term "dividing wall" refers to a partition disposed within an interior of a column to provide fractionation zones on either side of the dividing wall. Each dividing wall can be either segmented or continuous. A dividing wall is "continuous" if it extends between two points on the perimeter of a distillation column. Each dividing wall can be parallel or non-parallel relative to a longitudinal axis of the column. The fractionation zones can have the same or different cross-sectional areas, volumes, or both. Each dividing wall can also be non-insulated, partially insulated, or completely insulated. Exemplary dividing wall columns are described in U.S. Pat. Nos. 2,471,134; 5,755,933; 5,914,012; 6,347,533; 6,645,350; and 6,958,111.

As used herein, the term "externally supplied heat energy" refers to any heat energy source that is external to and not derived from components of the system, including without limitation components of the fractionation train, any hydrocarbon liquid feed fed to the fractionation train, or any components of any hydrocarbon liquid feed fed to the fractionation train. In other words, externally supplied heat energy does not arise from nor is it generated within the system. For example, heat energy input to the system from the compressor attached to the DIB does not qualify as "externally supplied heat energy" because the heat energy is generated within the system (via compression of the DIB overhead).

In all embodiments, the majority of all externally supplied heat energy supplied to the system is input to the system via the externally heated reboiler of the DWC. Preferably, 95% or more of the total externally supplied heat energy to the system for the primary purpose of driving fractionation of the hydrocarbons in the hydrocarbon liquid feed fed to the fractionation train is input to the system through the externally heated reboiler of the DWC. As used herein, "for the primary purpose of driving fractionation of the hydrocarbons in the hydrocarbon liquid feed" means that the sole or principal function of the externally supplied heat energy input to the system is for heating the hydrocarbon liquid feed components in the to facilitate separation or fractionation of the hydrocarbon components. It is understood that additional sources of externally supplied heat energy could be supplied to the system for purposes other than fractionation of the hydrocarbon liquid feed fed to the train. For example, externally supplied heat energy may be supplied to the system via mole sieve dryer regenerator heaters, amine regenerator reboilers, or other equipment principally configured to supply heat energy for other processes. In a preferred embodiment, 75% or more of all externally supplied heat energy supplied to the system for any purpose is input to the system via the externally heated reboiler of the DWC.

In addition to the externally supplied heat energy, sources of internally supplied heat energy include compression of the DIB overhead, any pumps used to transport the hydrocarbon liquid feed, and any sensible and/or latent heat attributable to one or more of the feed, product, column liquid and vapor draws, reboiler, or condenser streams.

The majority of all externally supplied heat is input to the system at only one point—the externally heated reboiler of the DWC. In all of the embodiments disclosed herein, the externally heated reboiler is configured to solely or principally function to provide externally supplied heat energy for purposes of driving fractionation of the hydrocarbons in the hydrocarbon liquid feed. The external heat supply of the externally heated reboiler directly supplies heat to the DWC and indirectly supplies heat to other portions and components of the system, including the deethanizer (when used) and DIB. In a preferred embodiment, the externally heated reboiler of the DWC is a furnace heated via combustion of externally supplied hydrocarbons and/or hydrogen. The flames from the combustion directly heat the tubes in which the DWC bottoms circulate through the firebox of the furnace. The external heat supply can alternatively be provided via externally heated heat transfer fluids that pass through the externally heated reboiler of the DWC for heat exchange with the bottoms of the DWC circulating through the reboiler. The heat transfer fluids are heated externally to temperatures greater than the process and are heated through interchange of hot gases and/or flames which are generated through the combustion of hydrocarbons and/or hydrogen. Exemplary heat transfer fluids include, but are not limited to, heavy hydrocarbons (C10+) and/or inorganic liquids, engineered heat transfer oils, steam and/or hot water.

As used herein, the term "deisobutanizer column" or DIB refers to any column utilized to separate i-butane from n-butane.

Figure 1:
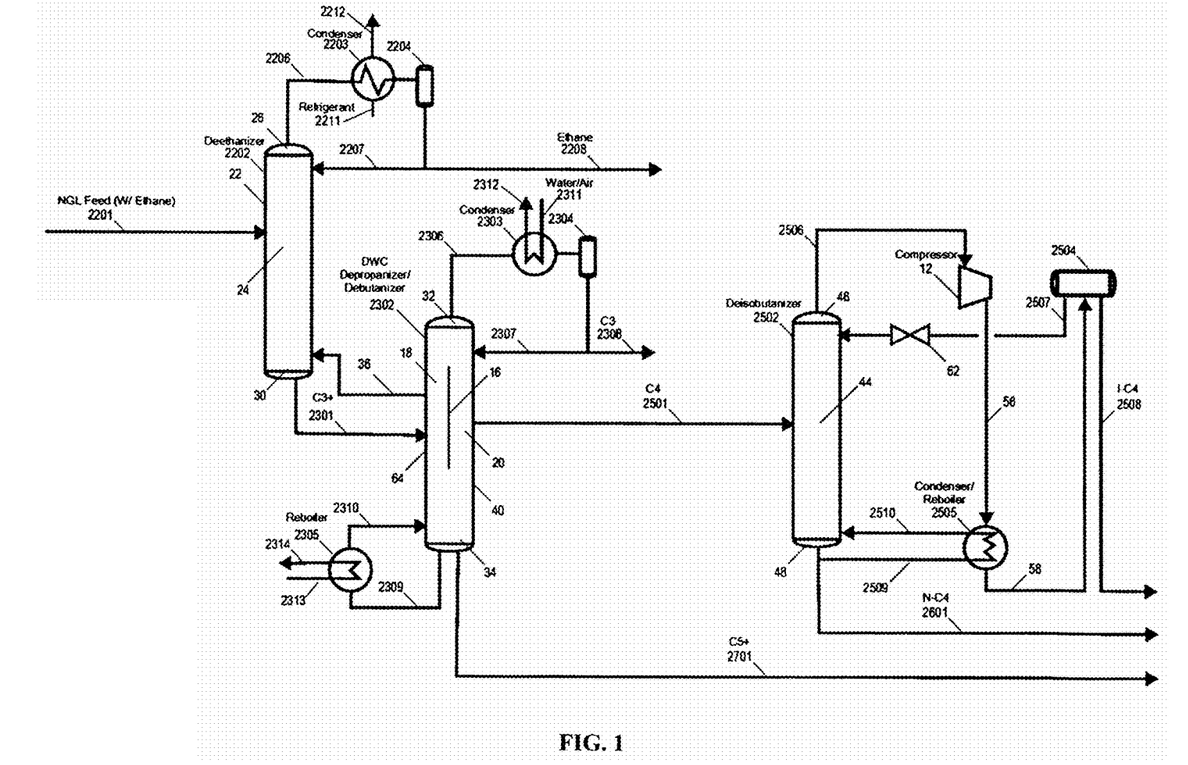
FIG. 1 depicts a process flow diagram of a system in accordance with a first embodiment of the present invention, wherein the system includes a deethanizer thermally coupled to a combined depropanizer and debutanizer dividing wall column followed by a deisobutanizer integrated with a compressor.

Referring now to FIG. 1, a fractionation train in accordance with a first embodiment of the invention is denoted by reference numeral 10. Fractionation train 10 includes the following distillation/fractionation columns: deethanizer 2202, depropanizer/debutanizer dividing wall column (DWC) 2302, and deisobutanizer (DIB) 2502. DWC 2302 includes a single dividing wall 16 which separates first fractionation zone 18 from second fraction zone 20. Condenser 2203 is connected to deethanizer 2202. Condenser 2303 and externally heated reboiler 2305 are connected to DWC 2302. Heat exchange reboiler 2505 and compressor 12 are connected to DIB 2502.

In this embodiment, DWC 2302 preferably has a circular cross-section and a single dividing wall 16 bisecting the cross-section of the column to provide fractionation zone 18 and 20 on each side of dividing wall 16. The dividing wall 16 is continuous, may or may not be insulated, and does not extend to the top and bottom of the DWC 2302. The length of the column extending above the top of the dividing wall 16 is sufficient to install apparatus to create a top or rectification section 32. The length of the column extending below the bottom of dividing wall 16 is sufficient to install apparatus to create a bottom or stripping section 34. The dividing wall 16 may have portions which run parallel and perpendicular to the longitudinal axis of the column so as to redistribute the cross-sectional area available for fractionation zones 18 and 20.

Fractionation train 10 can be utilized to fractionate a hydrocarbon liquid feed that primarily includes C2+ hydrocarbons as described herein. The hydrocarbon liquid feed stream with C2+ hydrocarbons is fed via deethanizer inlet 2201 in the feed side 22 of deethanizer 2202 into fractionation zone 24. Deethanizer 2202 is preferably operated at a temperature ranging between −20 and 220 degrees Fahrenheit and a pressure ranging between 135 and 350 psig. The ethane within the hydrocarbon liquid feed is vaporized in deethanizer 2202, causing it to travel overhead to the top or rectification section 26 and through overhead outlet 2206 as an ethane overhead product. The ethane overhead product is preferably in overhead outlet 2206 at a temperature ranging from −20 to 100 degrees Fahrenheit and a pressure ranging from 135 to 345 psig prior to entering condenser 2203. The ethane overhead product is then condensed in condenser 2203 with a heat transfer medium or refrigerant that travels through condenser 2203 via coolant inlet 2211 and coolant outlet 2212. The ethane overhead product travels through overhead outlet 2206 to one or more deethanizer reflux drums 2204, from which it can be removed. The ethane overhead product in reflux drum 2204 is a relatively pure product, preferably having an ethane content greater than 70%, most preferably 95% liquid volume (LV). At least a portion of the condensed ethane overhead product in reflux drum 2204 can be refluxed back into the top or rectification section 26 of deethanizer 2202 via reflux inlet 2207. The remainder of the condensed ethane overhead product in reflux drum 2204 may be removed as a relatively pure final product of ethane via ethane outlet 2208.

The liquid C3+ hydrocarbons of the hydrocarbon liquid feed travel down and out of deethanizer 2202 through bottom or stripping section 30 as a C3+ bottoms product via DWC inlet 2301. At least a portion of the liquid C3+ hydrocarbons are then fed through DWC inlet 2301 in the feed side 64 where they enter a first fractionation zone 18 of DWC 2302. DWC 2302 is preferably operated at a temperature ranging between 75 and 400 degrees Fahrenheit and a pressure ranging between 135 and 265 psig. All of the C3 hydrocarbons (propane) and some of the C4 hydrocarbons (n-butane and/or i-butane) in DWC 2302 travel up the first fractionation zone 18 as vapor to top or rectification section 32. At least a portion of this vapor can be fed to bottom or stripping section 30 of deethanizer 2202 via vapor outlet 36 in order to provide the column duty (i.e. to heat the interior of the deethanizer) for the fractionation occurring within deethanizer 2202. The column duty of deethanizer 2202 is thus transferred from DWC 2302 such that deethanizer 2202 is "thermally coupled" to DWC 2302. With this arrangement, deethanizer 2202 does not require a separate reboiler or other heat exchanger to heat deethanizer 2202. The remainder of the C4 and all of the C5+ hydrocarbons travel down DWC 2302 as liquid to bottom or stripping section 34 of DWC 2302.

At the top or rectification section 32 of DWC 2302, the propane vapor is separated from any remaining C4 (n-butane and i-butane) and travels through overhead outlet 2306 as a propane overhead product. The propane overhead product in overhead outlet 2306 is preferably at a temperature ranging from 75 to 125 degrees Fahrenheit and a pressure ranging from 120 to 250 psig prior to entering condenser 2303. When operated within that pressure range, air or water can be used to serve as a heat transfer medium that condenses the propane overhead product. The propane overhead product is then condensed in condenser 2303 with air or water that travels through condenser 2303 via coolant inlet 2311 and coolant outlet 2312. Once the propane overhead product is condensed in condenser 2203, it travels to one or more DWC reflux drums 2304 from which it can be removed. The propane overhead product in DWC reflux drum 2304 is relatively pure propane, preferably having a propane content greater than 85%, most preferably 95% liquid volume (LV). At least a portion of the propane overhead product in DWC reflux drum 2304 can be refluxed back to top or rectification section 32 of DWC 2302 through reflux inlet 2307. The remainder of the condensed propane in DWC reflux drum 2304 may be removed as a relatively pure final product of propane via propane outlet 2308.

The separation of C4 (n-butane and i-butane) from C3 (propane) occurs in the upper portion of second fractionation zone 20 of DWC 2302, while the separation of C4 from C5+ occurs in the lower section of second fractionation zone 20 of DWC 2302. A liquid DWC intermediate product that is primarily C4 (n-butane and i-butane) is drawn out of intermediate side 40 of DWC 2302 from second fractionation zone 20 and is fed into DIB inlet 2501. The liquid C5+ hydrocarbons are drawn off the bottom or stripping section 34 of DWC 2302 into C5+ outlet 2701 as a C5+ bottoms product that is a relatively pure product, preferably having a C5+ hydrocarbon content greater than 90%, most preferable 98% liquid volume (LV). The liquid or bottoms in bottom or stripping section 34 of DWC 2302 is heated with an externally heated reboiler 2305 on the sump of DWC 2302. At least a portion of the liquid bottoms in bottom or stripping section 34 of DWC 2302, which is mostly C5+ hydrocarbons, can be drawn into recycle inlet 2309, heated in externally heated reboiler 2305, and fed back to bottom or stripping section 34 of DWC 2302 through recycle outlet 2310. As discussed above, the externally heated reboiler 2305 can be a furnace that directly heats the bottoms circulating through the firebox of the furnace or a heat exchanger with an externally heated heat transfer medium exchanging heat with the bottoms liquid. The liquid in recycle outlet 2310 is preferably at a temperature ranging from 250 to 400 degrees Fahrenheit and a pressure ranging from 140 to 265 psig.

The DWC intermediate product in DIB inlet 2501 is fed to a fractionation zone 44 of DIB 2502 in order to separate i-butane from n-butane. DIB 2502 is preferably operated at a temperature ranging between 70 and 150 degrees and a pressure ranging between 35 and 90 psig. The i-butane is vaporized within fractionation zone 44 of DIB 2502, causing it to travel overhead to top or rectification section 46 and through overhead outlet 2506 as an i-butane overhead product. The i-butane overhead product in overhead outlet 2506 is preferably at a temperature ranging from 70 to 120 degrees Fahrenheit and a pressure ranging from 35 to 85 psig prior to entering compressor 12. The i-butane overhead product travels through overhead outlet 2506 and is compressed via compressor 12, thereby increasing the pressure such that it can transfer heat into the bottom of DIB 2502 through heat exchanger reboiler 2505. The compressed i-butane overhead product is then fed through heat exchange reboiler 2505 via heat exchange reboiler inlet 56 and heat exchange reboiler outlet 58. Simultaneously, at least a portion of the bottoms of DIB 2502 in bottom or stripping section 48, which is mostly n-butane, is drawn into recycle inlet 2509, heated in heat exchange reboiler 2505 through indirect contact with the compressed i-butane overhead product, and fed back to bottom or stripping section 48 of DIB 2502 through recycle outlet 2510. The indirect contact of the i-butane overhead product with at least a portion of the bottoms of DIB 2502 in heat exchange reboiler 2505 provides the heat exchange necessary to condense the compressed i-butane overhead product and vaporize the portion of the liquid bottoms, which in turn provides the heat energy needed in DIB 2502 for fractionation. The bottoms in recycle outlet 2510 is preferably at a temperature ranging from 90 to 150 degrees Fahrenheit and a pressure ranging from 40 to 90 psig. Once the i-butane overhead product is condensed, it travels through heat exchange reboiler outlet 58 to one or more i-butane reflux drums 2504, where it can be removed. The i-butane overhead product in i-butane reflux drum 2504 is relatively pure i-butane, preferably having an i-butane content greater than 90%, most preferably 96% liquid volume (LV). At least a portion of the condensed i-butane overhead product in i-butane reflux drum 2504 can be refluxed back to the top or rectification section 46 of DIB 2502 through reflux inlet 2507. As shown, the portion refluxed back to DIB 2502 through reflux inlet 2507 passes through an expansion valve 62 in order to adjust for the pressure of DIB 2502. Cooling with air, water, or refrigerant may occur on reflux inlet 2507 and/or i-butane outlet 2508. In one exemplary embodiment, a cooler (not shown) can be connected to reflux inlet 2507 upstream from expansion valve 62. The remainder of the condensed i-butane overhead product in i-butane reflux drum 2504 may be removed as a relatively pure final product of i-butane via i-butane outlet 2508. The liquid n-butane travels down DIB 2502 to the bottom or stripping section 48 of DIB 2502 and is drawn off the bottom or stripping section 48 through n-butane outlet 2601 as an n-butane bottoms product that is a relatively pure final product of n-butane, preferably having a n-butane content greater than 90%, most preferably 94% liquid volume (LV).

More refrigeration is required to condense the ethane overhead product of deethanizer 2202 than is typically required in fractionation trains of the prior art due to the fact that deethanizer 2202 is thermally coupled with DWC 2302, which causes deethanizer 2202 to operate at a lower operating pressure. However, this additional refrigeration cost is compensated for by the decrease in overall heat input, lower capital costs, and a reduced need for plot space. The scheme of fractionation train 10, with a larger refrigeration duty and cooler purity ethane product, may be more advantageous in cases where the ethane is to be fully liquefied at low pressure for storage or export as the energy cost associated with the first phase of refrigeration will already have to be paid for. Alternatively, if a cooler ethane product is not desirable, once pumped, it could be integrated back into the process by utilizing a side cooler in fractionation Zone 22, or a cooling in the externally provided refrigeration loop.

Figure 2:
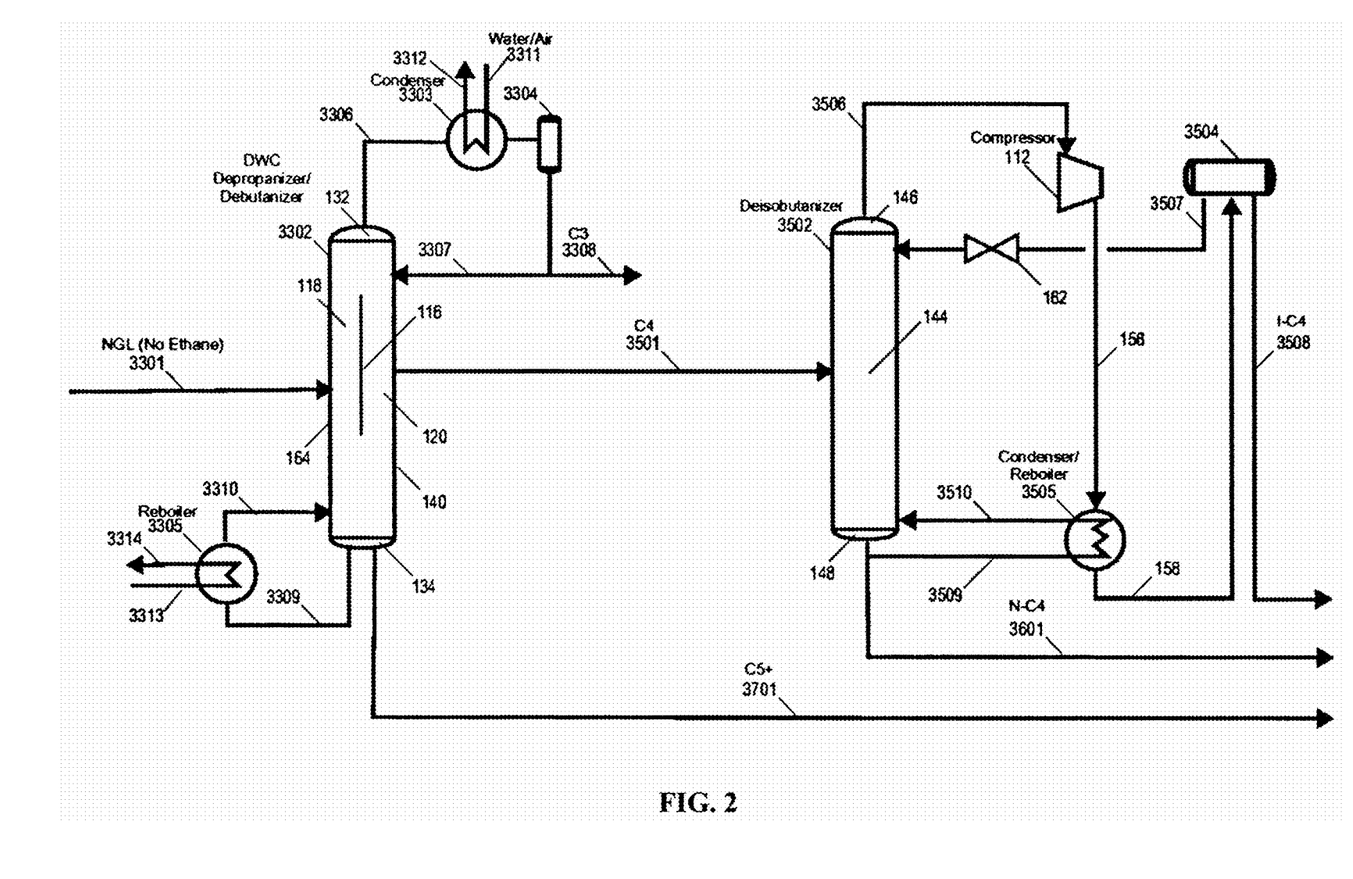
FIG. 2 depicts a process flow diagram of a system in accordance with a second embodiment of the present invention, wherein the system includes a combined depropanizer and debutanizer dividing wall column followed by a deisobutanizer integrated with a compressor.

Referring to FIG. 2, a fractionation train in accordance with a second embodiment of the invention is denoted by the numeral 110. Fractionation train 110 includes the following distillation/fractionation columns: depropanizer/debutanizer dividing wall column (DWC) 3302 and deisobutanizer (DIB) 3502. DWC 3302 includes a single dividing wall 116 which separates first fractionation zone 118 from second fractionation zone 120. Condenser 3303 and externally heated reboiler 3305 are connected to DWC 3302. Heat exchange reboiler 3505 and compressor 112 are connected to DIB 3502.

In this embodiment, DWC 3302 preferably has a circular cross-section and a single dividing wall 116 bisecting the cross-section of the column to provide fractionation zone 118 and 120 on each side of dividing wall 116. The dividing wall 116 is continuous, may or may not be insulated, and does not extend to the top and bottom of the DWC 3302. The length of the column extending above the top of the dividing wall 116 is sufficient to install apparatus to create a top or rectification section 132. The length of the column extending below the bottom of dividing wall 116 is sufficient to install apparatus to create a bottom or stripping section 134. The dividing wall 116 may have portions which run parallel and perpendicular to the longitudinal axis of the column so as to redistribute the cross sectional area available for fractionation zones 118 and 120.

Fractionation train 110 can be utilized to fractionate a hydrocarbon liquid feed that primarily includes C3+ hydrocarbons (little or no ethane is included) as described herein. Ethane could be removed from the hydrocarbon liquid feed either off site or where fractionation train 110 is installed downstream of a conventional deethanizer. A hydrocarbon liquid feed stream with C3+ hydrocarbons is fed via DWC inlet 3301 in the feed side 164 to first fractionation zone 118 of DWC 3302. DWC 3302 is preferably operated at a temperature ranging between 75 and 400 degrees Fahrenheit and a pressure ranging between 120 and 265 psig. All of the C3 (propane) and some of the C4 (n-butane and/or i-butane) in DWC 3302 travel up the first fractionation zone 118 as vapor to top or rectification section 132. The remainder of the C4 and all of the C5+ hydrocarbons travel down the column as liquid to bottom or stripping section 134 of DWC 3302.

At the top or rectification section 132 of DWC 3302, the propane vapor is separated from any remaining C4 (n-butane and i-butane) and travels through overhead outlet 3306 as a propane overhead product. The propane overhead product in overhead outlet 3306 is preferably at a temperature ranging from 75 to 125 degrees Fahrenheit and a pressure ranging from 120 to 260 psig prior to entering condenser 3303.

When operated within that pressure range, air or water can be used to serve as a heat transfer medium that condenses the propane overhead product. The propane overhead product is condensed in condenser 3303 with air or water that travels through condenser 3303 via coolant inlet 3311 and coolant outlet 3312. Once the propane overhead product is condensed in condenser 3303, it travels to one or more DWC reflux drums 3304 from which it can be removed. The propane overhead product in DWC reflux drum 3304 is relatively pure propane, preferably having a propane content greater than 85%, most preferably 95% liquid volume (LV). At least a portion of the propane overhead product in DWC reflux drum 3304 can be refluxed back to top or rectification section 132 of DWC 3302 via reflux inlet 3307. The remainder of the condensed propane overhead product in DWC reflux drum 3304 may be removed as a relatively pure final product of propane via propane outlet 3308.

The separation of C4 (n-butane and i-butane) from C3 (propane) occurs in the upper portion of second fractionation zone 120 of DWC 3302, while the separation of C4 from C5+ occurs in the lower section of second fractionation zone 120 of DWC 3302. A liquid DWC intermediate product that is primarily C4 (n-butane and i-butane) is drawn out of intermediate side 140 of DWC 3302 from second fractionation zone 120 and is fed through DIB inlet 3501. The liquid C5+ hydrocarbons are drawn off the bottom or stripping section 134 of DWC 3302 through C5+ outlet 3701 as a C5+ bottoms product that is a relatively pure product, preferably having a C5+ hydrocarbon content greater than 90%, most preferably 98% liquid volume (LV). The liquid or bottoms in the bottom or stripping section 134 of DWC 3302 is heated with an externally heated reboiler 3305 on the sump of DWC 3302. At least a portion of the liquid bottoms in stripping section 134 of DWC 3302, which is mostly C5+ hydrocarbons, can be drawn into recycle outlet 3309, heated in externally heated reboiler 3305, and fed back to bottom or stripping section 134 of DWC 3302 through recycle inlet 3310. As discussed above, the externally heated reboiler 3305 can be a furnace that directly heats the bottoms circulating through the firebox of the furnace or a heat exchanger with an externally heated heat transfer medium exchanging heat with the bottoms liquid. The liquid in recycle outlet 3310 is preferably at a temperature ranging from 250 to 400 degrees Fahrenheit and a pressure ranging from 125 to 265 psig.

The DWC intermediate product in DIB inlet 3501 is fed to a fractionation zone 144 of DIB 3502 in order to separate i-butane from n-butane. DIB 3502 is preferably operated at a temperature ranging between 70 and 150 degrees Fahrenheit and a pressure ranging between 35 and 90 psig. The i-butane is vaporized within fractionation zone 144 of DIB 3502, causing it to travel overhead to top or rectification section 146 and through overhead outlet 3506 as an i-butane overhead product. The i-butane overhead product in overhead outlet 3506 is preferably at a temperature ranging from 70 to 120 degrees Fahrenheit and a pressure ranging from 35 to 85 psig prior to entering compressor or compressor 112. The i-butane overhead product travels through overhead outlet 3506 and is compressed via compressor 112, thereby increasing the pressure such that it can transfer heat into the bottom of DIB 3502 through heat exchange reboiler 3505. The compressed i-butane overhead product is then fed through heat exchange reboiler 3505 via heat exchange reboiler inlet 156 and heat exchange reboiler outlet 158. Simultaneously, at least a portion of the bottoms of DIB 3502 in bottom or stripping section 148, which is mostly n-butane, is drawn into recycle inlet 3509, heated in heat exchange reboiler 3505 through indirect contact with the compressed i-butane overhead product, and fed back to bottom or stripping section 148 of DIB 3502 through recycle outlet 3510. The indirect contact of the i-butane overhead product with at least a portion of the bottoms of DIB 3502 in heat exchange reboiler 3505 provides the heat exchange necessary to condense the compressed i-butane overhead product and vaporize the portion of the liquid bottoms, which in turn provides the heat energy needed in the DIB 3502 for fractionation. The bottoms in recycle outlet 3510 is preferably at a temperature ranging from 90 to 150 degrees Fahrenheit and a pressure ranging from 40 to 90 psig. Once the i-butane overhead product is condensed, it travels through heat exchange reboiler outlet 158 to one or more i-butane reflux drums 3504, where it can be removed. The i-butane overhead product in i-butane reflux drum 3504 is relatively pure i-butane, preferably having an i-butane content greater than 90%, most preferably 96% liquid volume (LV). At least a portion of the condensed i-butane overhead product in i-butane reflux drum 3504 can be refluxed back to the top or rectification section 146 of DIB 3502 through reflux inlet 3507. As shown, the portion refluxed back to DIB 3502 through reflux inlet 3507 passes through an expansion valve 162 in order to adjust for the pressure of DIB 3502. Cooling with air, water, or refrigerant may occur on reflux inlet 3507 and/or i-butane outlet 3508. In one exemplary embodiment, a cooler (not shown) can be connected to reflux inlet 3507 upstream from expansion valve 162. The remainder of the condensed i-butane overhead product in i-butane reflux drum 3504 may be removed as a relatively pure final product of i-butane via i-butane outlet 3508. The liquid n-butane travels down DIB 3502 to the bottom or stripping section 148 of DIB 3502 and is drawn off the bottom or stripping section 148 through n-butane outlet 3601 as an n-butane bottoms product that is a relatively pure final product of n-butane, preferably having a n-butane content greater than 90%, most preferably 94% liquid volume (LV).

Figure 3:
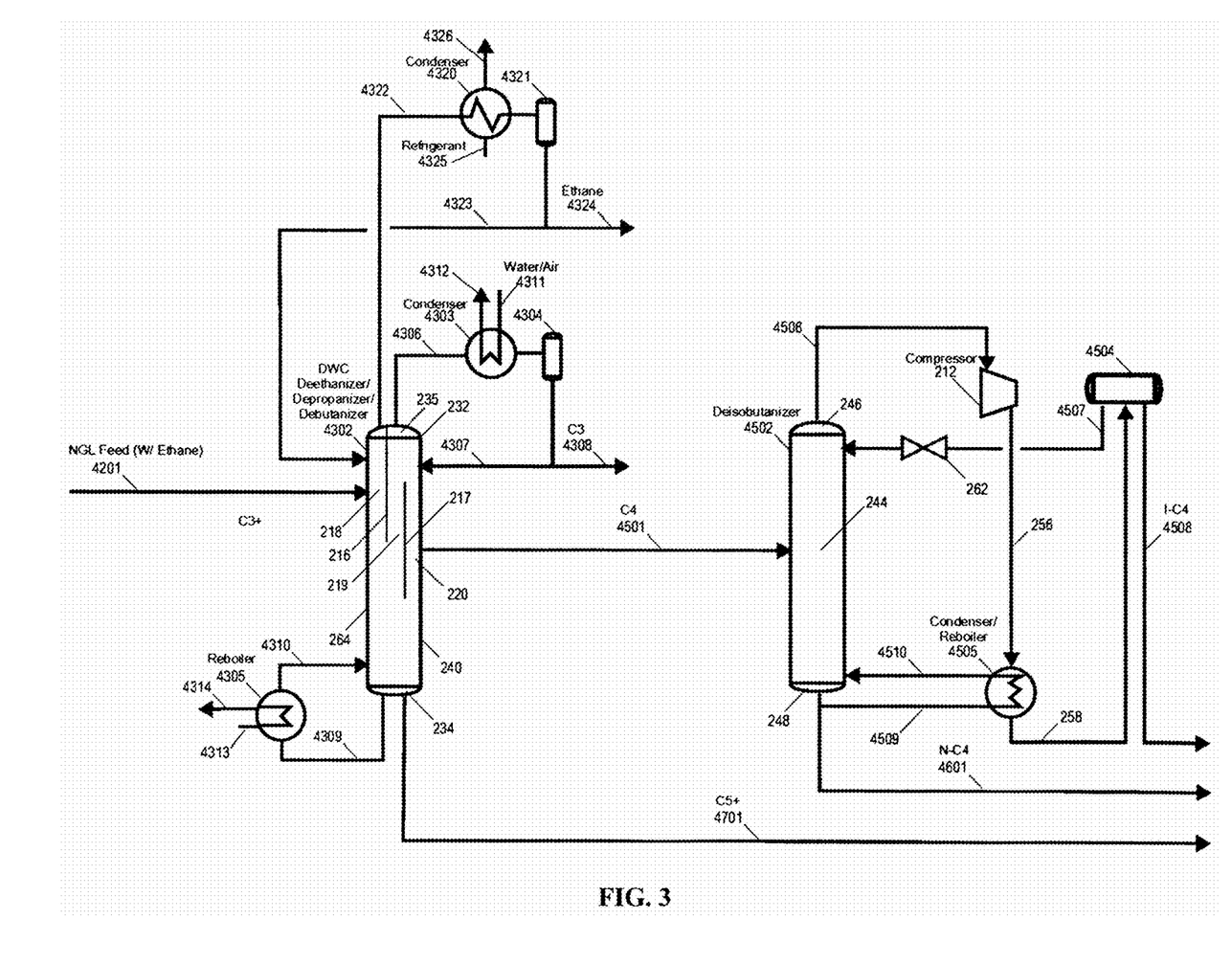
FIG. 3 depicts a process flow diagram of a system in accordance with a third embodiment of the present invention, wherein the system includes a combined deethanizer, depropanizer, and debutanizer double dividing wall column followed by a deisobutanizer integrated with a compressor.

Referring to FIG. 3, a fractionation train in accordance with a third embodiment of the present invention is denoted by numeral 210. Fractionation train 210 includes the following distillation/fractionation columns: deethanizer/depropanizer/debutanizer dividing wall column (DWC) 4302 and deisobutanizer (DIB) 4502. DWC 4302 includes two dividing walls 216 and 217 which form three fractionation zones within DWC 4302: first fractionation zone 218, second fractionation zone 219, and third fractionation zone 220. Dividing wall 216 extends to the top of DWC 4302, thereby separating the top or rectification section 232 into a deethanizer zone 233 and a depropanizer zone 235, which in turn allows for the production of separate overhead vapor streams 4306 and 4322. Condensers 4303 and 4320 and externally heated reboiler 4305 are connected to DWC 4302. Heat exchange reboiler 4505 and compressor 212 are connected to DIB 4502.

In this embodiment, DWC 4302 preferably has a circular cross-section and two dividing walls that provide cross-sectional areas that correspond to the liquid and vapor loads within each of three fractionation zones 218, 219, and 220. Dividing walls 216 and 217 are continuous and may or may not be insulated. Dividing wall 217 extends from above the bottom of dividing wall 216 but not to the top of DWC 4302 leaving room for depropanizer zone 235. Dividing wall 217 extends down below the elevation of the bottom of 216 but not to the bottom of DWC 4302 leaving room for stripping section 234.

Fractionation train 210 can be utilized to fractionate a hydrocarbon liquid feed that primarily includes C2+ hydrocarbons as described herein. A hydrocarbon liquid feed stream with C2+ hydrocarbons is fed via DWC inlet 4201 in the feed side 264 of DWC 4302 to first fractionation zone 218 of DWC 4302. DWC 4302 is preferably operated at a temperature ranging between −20 and 400 degrees Fahrenheit and a pressure ranging between 120 and 350 psig. All of the C2 (ethane) within the hydrocarbon liquid feed is vaporized in the first fractionation zone 218 causing it to travel overhead to deethanizer rectification section 233 of DWC 4302 and through overhead outlet 4322 as an ethane overhead product. The ethane overhead product is then condensed in condenser 4320 with a refrigerant that travels through condenser 4320 via coolant inlet 4325 and coolant outlet 4326. The ethane overhead product then travels through overhead outlet 4322 to one or more ethane reflux drums 4321, where it may be removed. The ethane overhead product in ethane reflux drum 4321 is relatively pure ethane, preferably having an ethane content greater than 70%, most preferably 95% liquid volume (LV). At least a portion of the condensed ethane overhead product in ethane reflux drum 4321 can be refluxed back to the top or rectification section 232 in the fractionation zone 218 of DWC 4302 via reflux inlet 4323. The remainder of the condensed ethane overhead product in ethane reflux drum 4321 may be removed as a relatively pure final product of ethane via ethane outlet 4324.

The liquid C3+ hydrocarbons of the hydrocarbon liquid feed travel down the first fractionation zone 218 and below the first dividing wall 216. All of the C3 (propane) and some of the C4 (n-butane and/or i-butane) travel up the second fractionation zone 219 as vapor to depropanizer zone 235. The remainder of the C4 and all of the C5+ hydrocarbons travel down to the bottom or stripping section 234 of DWC 4302 as liquid. At the top of DWC 4302 in the portions of the second and third fractionation zones 219 and 220 that are located above second dividing wall 217, the propane vapor is separated from any remaining C4 (n-butane and i-butane) and travels up to depropanizer zone 235 and through overhead outlet 4306 as a propane overhead product. The propane overhead product in overhead outlet 4306 is preferably at a temperature ranging from 75 to 125 degrees Fahrenheit and a pressure ranging from 120 to 345 psig prior to entering condenser 4303. When operated within that pressure range, air or water can be used to serve as a heat transfer medium that condenses the propane overhead product. The propane overhead product vapor is then condensed in condenser 4303 with air or water that travels through condenser 4303 via coolant inlet 4311 and coolant outlet 4312. Once the propane overhead product is condensed in condenser 4303, it travels to one or more DWC reflux drums 4304, where it can be removed. The propane overhead product in DWC reflux drum 4304 is relatively pure propane, preferably having a propane content greater than 85%, most preferably 95% liquid volume (LV). At least a portion of the condensed propane overhead product in DWC reflux drum 4304 can be refluxed back to the top or rectification section 232 in the depropanizer zone 235 of DWC 4302 via reflux inlet 4307. The remainder of the condensed propane overhead product in DWC reflux drum 4304 may be removed as a relatively pure final product of propane via propane outlet 4308.

The separation of C4 (n-butane and i-butane) from C3 (propane) occurs in the upper portion of third fractionation zone 220 of DWC 4302, while the separation of C4 from C5+ occurs in the bottom or stripping section 234 of DWC 4302. A liquid DWC intermediate product that is primarily C4 (n-butane and i-butane) is drawn out of intermediate side 240 of DWC 4302 from third fractionation zone 220 and is fed into DIB inlet 4501. The liquid C5+ hydrocarbons are drawn off the bottom or stripping section 234 of DWC 4302 into C5+ outlet 4701 as a C5+ bottoms product that is a relatively pure product, preferably having a C5+ hydrocarbon content greater than greater than 90%, most preferable 98% liquid volume (LV). The liquid or bottoms in the bottom or stripping section 234 of DWC 4302 is heated with a single externally heated reboiler 4305 on the sump of DWC 4302. At least a portion of the liquid in bottom or stripping section 234 of DWC 4302, which is mostly C5+ hydrocarbons, can be drawn into recycle inlet 4309, heated in externally heated reboiler 4305, and fed back to bottom or stripping section 234 of DWC 4302 through recycle outlet 4310. As discussed above, the externally heated reboiler 4305 can be a furnace that directly heats the bottoms circulating through the firebox of the furnace or a heat exchanger with an externally heated heat transfer medium exchanging heat with the bottoms liquid. The liquid in recycle outlet 4310 is preferably at a temperature ranging from 250 to 400 degrees Fahrenheit and a pressure ranging from 125 to 350 psig.

The DWC intermediate product in DIB inlet 4501 is fed to a fractionation zone 244 of DIB 4502 in order to separate i-butane from n-butane. DIB 4502 is preferably operated at a temperature ranging between 70 and 150 degrees Fahrenheit and a pressure ranging between 35 and 90 psig. The i-butane is vaporized within fractionation zone 244 of DIB 4502, causing it to travel overhead to top or rectification section 246 and through overhead outlet 4506 as an i-butane overhead product. The i-butane overhead product in overhead outlet 4506 is preferably at a temperature ranging from 70 to 120 degrees Fahrenheit and a pressure ranging from 35 to 85 psig prior to entering compressor 212. The i-butane overhead product travels through overhead outlet 4506 and is compressed via compressor 212, thereby increasing the pressure such that it can transfer heat into the bottom of the column through heat exchange reboiler 4505. The compressed i-butane overhead product is then fed through heat exchange reboiler 4505 via heat exchange reboiler inlet 256 and heat exchange reboiler outlet 258. Simultaneously, at least a portion of the bottoms of DIB 4502 in bottom or stripping section 248, which is mostly n-butane, is drawn into recycle inlet 4509, heated in heat exchange reboiler 4505 through indirect contact with the compressed i-butane overhead product, and fed back to bottom or stripping section 248 of DIB 4502 through recycle outlet 4510. The indirect contact of the i-butane overhead product with at least a portion of the bottoms of DIB 4502 in heat exchange reboiler 4505 provides the heat exchange necessary to condense the compressed i-butane overhead product and vaporize the portion of the liquid bottoms, which in turn provides the heat energy needed in the DIB 4502 for fractionation. The bottoms in recycle outlet 4510 is preferably at a temperature ranging from 90 to 150 degrees Fahrenheit and a pressure ranging from 40 to 90 psig. Once the i-butane overhead product is condensed, it travels through heat exchange reboiler outlet 258 to one or more i-butane reflux drums 4504, where it can be removed. The i-butane overhead product in i-butane reflux drum 4504 is relatively pure i-butane, preferably having an i-butane content greater than 90%, most preferably 96% liquid volume (LV). At least a portion of the condensed i-butane overhead product in i-butane reflux drum 4504 can be refluxed back to top or rectification section 246 of DIB 4502 through reflux inlet 4507. As shown, the portion refluxed back to DIB 3502 through reflux inlet 4507 passes through an expansion valve 262 in order to adjust for the pressure of DIB 4502. Cooling with air, water, or refrigerant may occur on reflux inlet 4507 and/or i-butane outlet 4508. In one exemplary embodiment, a cooler (not shown) can be connected to reflux inlet 4507 upstream from expansion valve 262. The remainder of the condensed i-butane overhead product in i-butane reflux drum 4504 may be removed as a relatively pure final product of i-butane via i-butane outlet 4508. The liquid n-butane travels down DIB 4502 to the bottom or stripping section 248 of DIB 4502 and is drawn off bottom section 248 through n-butane outlet 4601 as an n-butane bottoms product that is a relatively pure final product of n-butane, preferably having a n-butane content greater than 90%, most preferably 94% liquid volume (LV).

More refrigeration is required to condense the ethane overhead product of DWC 4302 than is typically required in fractionation trains of the prior art due to the fact that the separations of C2, C3, and C4 all occur within a single DWC 4302 as opposed to multiple distillation columns, which causes first fractionation section 218 of DWC 4302 to operate at a lower operating pressure. However, this additional refrigeration cost is compensated for by the decrease in overall heat input, lower capital costs, and a reduced need for plot space. The scheme of fractionation train 210, with a larger refrigeration duty and cooler purity ethane product, may be more advantageous in cases where the ethane is to be fully liquefied at low pressure for storage or export as the energy cost associated with the first phase of refrigeration will already have to be paid for. Alternatively, if a cooler ethane product is not desirable, once pumped, it could be integrated back into the process by utilizing a side cooler in fractionation zone 22, or as cooling in the externally provided refrigeration loop.

It should be understood that although fractionation trains 10, 110, and 210 are each shown with only one condenser for each individual overhead product stream and only one reboiler for some of the distillation columns, it is within the scope of the present invention to utilize two or more condensers for a given overhead product stream or two or more reboilers for a given distillation column. Furthermore, the "externally heated reboiler" of the DWC is not limited to a single reboiler apparatus and may include multiple externally heated reboiler components, provided all of the components supply heated bottoms to the DWC.

From the foregoing it will be seen that this invention is one well adapted to attain all ends and objectives hereinabove set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A process for fractionating a liquid feed comprising hydrocarbons, the process comprising the steps of:

feeding a liquid feed to a dividing wall column wherein the liquid feed comprises hydrocarbons selected from the group consisting of C2, C3, C4, C5+, and combinations thereof;

heating at least a portion of a DWC bottoms liquid of the dividing wall column with an externally heated reboiler to supply a majority of all externally supplied heat for the process to the dividing wall column;

feeding at least a portion of a DWC intermediate comprising C4 hydrocarbons from the dividing wall column into a deisobutanizer column;

compressing at least a portion of an overhead vapor of the deisobutanizer column to form a compressed overhead and circulating the compressed overhead through a heat exchange reboiler to condense the compressed overhead;

circulating at least a portion of a DIB bottoms liquid of the deisobutanizer column through the heat exchange reboiler to heat the DIB bottoms liquid and returning the heated DIB bottoms liquid to the deisobutanizer column; and recovering one or more products from the dividing wall column and/or the deisobutanizer column, wherein the one or more products comprise relatively pure hydrocarbons and/or one or more combinations of hydrocarbons.

2. The process of claim 1, wherein the liquid feed comprises a natural gas liquid feed.

3. The process of claim 1, wherein the liquid feed comprises C2+ hydrocarbons.

4. The process of claim 1, wherein the liquid feed comprises C3+ hydrocarbons.

5. The process of claim 1, wherein the process further comprises the step of:

recovering a DWC overhead comprising C3 hydrocarbons from the dividing wall column as a propane product.

6. The process of claim 1, wherein the process further comprises the step of:

recovering a DWC bottoms comprising C5+ hydrocarbons from the dividing wall column.

7. The process of claim 1, wherein the process further comprises the step of:

recovering a DIB overhead comprising isobutane from the deisobutanizer column as an isobutane product; and recovering a DIB bottoms comprising n-butane from the deisobutanizer column as an n-butane product.

8. The process of claim 5, wherein the step of recovering a DWC overhead comprising C3 hydrocarbons from the dividing wall column as a propane product comprises condensing a DWC overhead comprising hydrocarbons with a condenser using cooling water, air, and/or combinations thereof.

9. The process of claim 3, wherein the process further comprises the steps of:

feeding a liquid comprising C2 hydrocarbons to a deethanizer column;

recovering a deethanizer overhead comprising C2 hydrocarbons from the deethanizer column as an ethane product; and feeding at least a portion of a deethanizer bottoms to the dividing wall column as the liquid feed.

10. The process of claim 9, wherein the process further comprises the step of:

feeding a portion of a vapor from the dividing wall column to a bottom of the deethanizer.

11. The process of claim 10, wherein the step of recovering a deethanizer overhead comprising C2 hydrocarbons comprises condensing the deethanizer overhead with a condenser using a refrigerant.

12. The process of claim 1, wherein the process additionally comprises the step of:
  recovering a second DWC overhead comprising C2 hydrocarbons from the dividing wall column as an ethane product.

13. The process of claim 12, wherein the step of recovering a second DWC overhead comprising C2 hydrocarbons from the dividing wall column as an ethane product comprises condensing the second DWC overhead comprising C2 hydrocarbons with a condenser using a refrigerant.

* * * * *